(12) United States Patent
Yu et al.

(10) Patent No.: US 7,638,555 B2
(45) Date of Patent: Dec. 29, 2009

(54) PHOTOCATALYTIC NANO-CRYSTALLINE $TIO_2$ THIN FILMS, METHOD FOR PREPARING THE SAME AND USE THEREOF

(75) Inventors: Chai-Mei Jimmy Yu, Hong Kong (CN); Jun Lin, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 777 days.

(21) Appl. No.: 10/688,504

(22) Filed: Oct. 17, 2003

(65) Prior Publication Data
US 2004/0202723 A1   Oct. 14, 2004

(30) Foreign Application Priority Data
Oct. 28, 2002   (CN)   ................. 02 1 47089

(51) Int. Cl.
*A01N 55/00* (2006.01)
*A01N 55/02* (2006.01)
*A01N 59/16* (2006.01)
*A61K 31/28* (2006.01)

(52) U.S. Cl. ...................... 514/492; 424/617
(58) Field of Classification Search ........................ None
See application file for complete search history.

(56) References Cited

U.S. PATENT DOCUMENTS 3,002,854 A * 10/1961 Brill ..................... 156/309.3
3,017,282 A * 1/1962 Brill ...................... 106/287.19
4,993,354 A * 2/1991 Makita et al. .............. 118/407
5,897,958 A * 4/1999 Yamada et al. ............. 446/474
6,106,955 A * 8/2000 Ogawa et al. ............... 428/469

OTHER PUBLICATIONS

Stathatos et al.. Nanocrystallite Titanium Dioxide Films Made by the Sol-Gel Method Using Reverse Micelles. Journal of Sol-Gel Science and Technology (1997), vol. 10, pp. 83-89.*
English abstract of CN 1312337 (Sep. 12, 2001).
English abstract of CN 1342517 (Apr. 3, 2002).
English abstract of CN 1400186 (Mar. 5, 2003).

* cited by examiner

*Primary Examiner*—Johann R Richter
*Assistant Examiner*—James H Alstrum Acevedo
(74) *Attorney, Agent, or Firm*—Knobbe Martens Olson & Bear LLP

(57) ABSTRACT

The preferred embodiments provide for a process for preparing a $TiO_2$ thin film. The preferred embodiments also provide for $TiO_2$ thin films prepared by the process herein, and a method of using $TiO_2$ thin films for killing bacteria and viruses in an environment under ultraviolet irradiation. The $TiO_2$ thin films according to the invention have higher photocatalytic activity, and can particularly be used to photocatalytically degrade organic pollutants in air to hereby kill bacteria and viruses therein.

14 Claims, 4 Drawing Sheets

PHOTOCATALYTIC NANO-CRYSTALLINE TIO$_2$ THIN FILMS, METHOD FOR PREPARING THE SAME AND USE THEREOF

BACKGROUND OF THE INVENTION

1. Field of the Invention

The invention relates to a method for preparing nano-crystalline TiO$_2$ thin films, and to environmental applications, particularly to the use of the nano-TiO$_2$ thin films under ultraviolet irradiation in killing bacteria and viruses in the environment.

2. Description of the Related Art

It is always a challenge to remove organic pollutants in air and to kill the bacteria and viruses in the environment in the fields of environmental science and medicine. In modern society, various organic pollutants and a great number of bacteria and viruses fill the crowded offices, shopping malls and public places. The health of people who live and work under such environments will obviously be affected.

It is known that TiO$_2$ semiconductors can effectively decompose organic pollutants in air and water under ultraviolet and kill bacteria therein. Therefore, a simple and feasible way is to have nano-crystalline TiO$_2$ immobilized on the surface of a substrate such as glass, metals and constructive materials, and then expose the substrate under ultraviolet to catalytically kill bacteria.

There have been many processes disclosed to fix TiO$_2$ to the substrate of glass, metals and ceramics, such as chemical vapor deposition, magnetic spraying, high speed spinning coating and pyrolysis. TiO$_2$ thin films prepared by these processes exhibit very poor photocatalytic and antibacterial activities or are easy to peel off from the substrate for the reasons that the TiO$_2$ thin films have poor crystallinity (even non-crystalline), and poor adhesivity with substrates to which they attach.

Chinese patent application No. 01128306.8 filed on Jul. 31, 2001 and published as CN 1400186A, on Mar. 5, 2003. As such, this patent application is not believed to qualify as prior art to the present application which has a priority date of Oct. 28, 2002. The application discloses a process for improving photocatalytic activities of TiO$_2$ thin films on glass. The process includes preparing a sol gel of TiO$_2$, coating the thin film on glass, treating the thin film using an acid, washing the treated thin film, and drying the thin film. The sol-gel is prepared by hydrolysis of titanium alkoxide. A stabilizer selected from triethanolamine, diethanolamine etc is used in preparation of the sol-gel.

Chinese patent application No. 01130896.6 filed on Aug. 31, 2001 and published on Apr. 3, 2002, discloses a process for preparing photo-catalysts of Meso-TiO$_2$ thin films. The process includes preparing a sol gel solution that is made from a titanium alkoxide or a titanium chloride, lower alkanol diethanolamine, water and polyethylene glycol having a molecular weight from 200 to 4,000; coating a thin film on a substrate by spinning coating or dip coating; and drying and calcining the thin film.

Chinese patent application No. 0110064.8 filed on Mar. 29, 2001 and published on Sep. 12, 2001, discloses a process for preparing a thin film of TiO$_2$ on a substrate. The process includes stirring a solution consisting of titanium alkoxide, ethanol amines and ethanol; adding to the solution a fluorine-containing compound or an aqueous solution of transitional metals, and coating a thin film on the substrate.

It is known that photocatalytic and antibacterial activities, and hydrophilicity of a TiO$_2$ thin film are significantly influenced by its phase constitutions, specific surface area, and porous size and distribution. It is understood that the above parameters of a TiO$_2$ thin film are affected by the process for preparing the same. Therefore, the process for preparing a thin film will significantly affect the photocatalytic activity of the TiO$_2$ thin film. The inventors, after conducting careful investigations, have found out that the reverse micelle technique is an effective method for preparing TiO$_2$ thin films with high photocatalytic activities. Moreover, a thin film prepared by the reverse micelle solution shows higher photocatalytic activity than those prepared by other processes in the prior art. The present invention is hereby provided. The TiO$_2$ thin film provided by the present invention is suitably used to photocatalytically decompose organic pollutants in air and thereby to kill bacteria and viruses in an environment.

SUMMARY OF THE INVENTION

Accordingly, an object of the invention is to provide a method for preparing a TiO$_2$ thin film having anti-bacterial, fungicidal, and/or antivirus activities. The method of the invention comprises the steps of:

a) providing a reverse micelle solution containing highly-dispersed water nano-droplets, which is made from an organic continuous phase, a non-ionic surfactant and water;

b) adding an alkyl titanate to the reverse micelle solution and subjecting titanium alkoxide to being hydrolyzed in said nano-droplets of the reverse micelle solution to form a TiO$_2$-containing solution;

c) forming a wet film onto a substrate dipped into the TiO$_2$-containing solution by a dip coating technique; and d) drying the wet film and calcining the dried film.

Another object of the invention is to provide a nano-crystalline TiO$_2$ thin film prepared by the process of the invention. Nano-crystalline materials generally are polycrystalline materials that have grain sizes less than one micron, more preferably no more than about 100 nm.

Still another object of the invention is to provide a method for killing bacteria and viruses in an environment, which comprises the steps of:

a) coating a TiO$_2$ thin film containing nano-crystalline TiO$_2$ on to a substrate by a reverse micelle method; and b) placing said TiO$_2$ thin film in the environment under ultraviolet irradiation.

Compared with the prior art, the invention has many advantages that the TiO$_2$ thin film can be formed onto all kinds of substrates in various shapes without any specific manufacturing apparatus; the TiO$_2$ thin film can be readily doped with other components by coating essential components for the TiO$_2$ thin film of the invention together with the other components; the TiO$_2$ particle's size in the thin film can be controlled by changing the molar ratio between the surfactant and water in the reverse micelle solution; the phase constitutions can be controlled by the thermal treatment of the thin film; and the thin film of the invention has a larger specific area and a higher activity of killing bacteria and viruses due to the nano-structure thereof.

DETAILED DESCRIPTION OF THE PREFERRED EMBODIMENT

Figure 1:
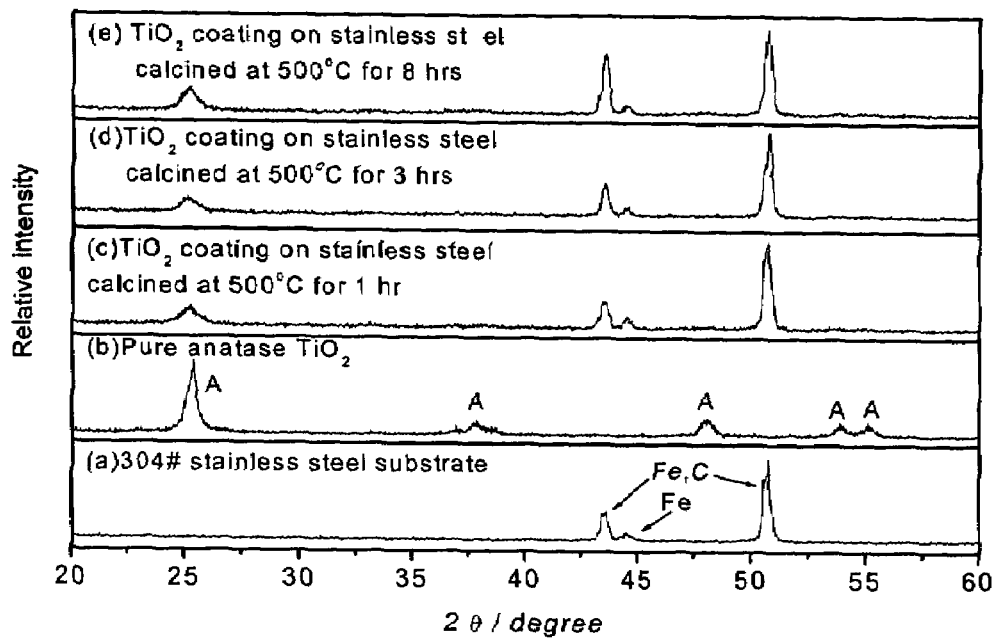
FIG. 1 is polycrystalline X-ray diffraction patterns of TiO$_2$ thin films of the present invention on stainless steel calcined for different periods of time.

In the process for preparing $TiO_2$ thin films of the invention, organic continuous phases may be liquid non-polar or lower-polar organic solvents at the ambient temperature. Examples of the organic continuous phases may include: unsubstituted alkanes or alkanes substituted with one or more substituents (substituting groups), unsubstituted alkenes or alkenes substituted with one or more substituents, unsubstituted alkynes or alkynes substituted with one or more substituents, and unsubstituted aromatic hydrocarbons or aromatic hydrocarbons substituted with one or more substituents. The substituents or substituting groups used herein includes, but not limited to, lower alkyl, halide, lower alkoxyl, cyanide, nitro and the like. The number of the substituents may be from 1 to 3, and preferably it is 1.

Unless specifically indicated otherwise, alkane, alkene and alkyne used in the invention include both straight chain or branch chain and cyclic alkane, alkene, and alkyne. In the invention, the continuous organic phase is selected $C_{3-8}$ alkane, and preferably $C_{5-6}$ cycloalkane, and more preferably cyclohexane.

In the invention, non-ionic surfactants used include polyols partial fatty acid esters, poly oxyethylene aliphatic alcohol ether, polyoxyethylene alkyl phenol ether, TRITON series (octylphenol ethoxylates). In the invention, Triton series such as TRITON™ X-100 and TRITON™ X-405 are preferably surfactants, of which TRITON™ X-100 is more preferable.

In the invention, alkyl titanate has the same meaning as "titanium alkoxide". The alkyl titanate according to the invention is selected from those that can be easily hydrolyzed to $TiO_2$ in the reverse micelles. Alkyl portion in alkyl titanate may be selected from $C_{1-6}$ alkyl, more preferably from $C_{2-4}$ alkyl, and most preferably ethyl and iso-propyl.

The concentration of the non-ionic surfactant in the reverse micelle solution is generally from 0.15 to 0.4M, and preferably 0.2M. The concentration of titanium alkoxide in the reverse micelle solution of the invention is generally from 0.1 to 0.4M, and more preferably from 0.2 to 0.3M. The molar ratio of water to the surfactant used in the invention may be between 1.0 and 3.0.

In addition, a small amount of a stabilizer can be added to the reverse micelle solution to control the rate of hydrolysis of the titanium alkoxide. In the invention, organic compounds of 2,4-diketone may be used as the stabilizer of the invention. It is well-known for those skilled in the art to select a proper stabilizer in the invention and the amount thereof. In general, the amount of the stabilizer used in the invention is ranged from 1 to 10% by volume of the reverse micelle solution. Preferably, acetyl acetone is used in the invention and accounts for 2 to 5% by volume in the reverse micelle solution.

The dip coating technique used in the process of the invention is the same as that well-known for those skilled in the art. Detailed information on the dip coating technique can be referred to R. Reisfeld and C. K. Jorgensen, 77 Structure and Bonding; Chemistry: Spectroscopy and Applications of Sol-gel Glass, Springer-Verlag, 1992, Berlin, pp 91-95.

The withdrawal speed in step c) can be adjusted based on the roughness of the substrate surface. The speed is normally set at 2-5 mm/s.

The drying temperature of the wet film in step d) is in general at 80°-120° C., and preferably at 100° C. for 0.5-1.5 hours. In this step, the dried film may be calcined at a temperature ranging from 500° to 650° C. and preferably at 600° C. The dried film may be calcined for 1 to 6 hours and preferably 1 to 3 hours.

Substrates used in the invention may be any objects in various shapes. Examples of the substrates include metal, glass, ceramics and the like. Stainless steel is a preferable substrate in the invention. It is believed that the reason lies in Fe ion in the stainless steel can be diffused into $TiO_2$ thin film when calcined, and the presence of Fe (III) will help charge separation and avoid the recombination of the electrons with holes.

In the invention, after the substrate is dipped into the reverse micelle solution, a homogenous $TiO_2$ sol-gel layer is formed onto the surface of the substrate with the dip coating technique. A homogenous mesoporous $TiO_2$ crystalline thin film will be formed after being calcined.

The substrate used in the invention is preferably cleaned before thin films are coated to achieve a good affinity between the $TiO_2$ thin film and the substrate.

The invention will be further described by the following examples.

Example 1

Preparation of $TiO_2$ Thin Films onto the Surface of Stainless Steel

To 100 ml of cyclohexane was added TRITON™ X-100 octylphenol ethoxylate, water, and resultant mixture was stirred for 2 hours to obtain a reverse micelle solution. In the solution, the concentration of TRITON™ X-100 ranged from 0.15 to 0.3M, and the ratio between water and TRITON™ X-100 was 2. In this Example, isopropyl titanate together with 5 ml of acetyl acetone was added to the reverse micelle solution. The concentration of the titanate was 0.2M. After resultant solution was continuously stirred for about 1 hour to have isopropyl titanate hydrolyzed in nano-droplets of the reverse micelle solution, the solution became homogeneous and optically transparent. Stainless steel of Type 304 was then dipped into the reverse micelle solution and a wet $TiO_2$ film was formed onto the stainless steel by the withdrawing technique, or which the withdrawal speed was controlled at 4 mm/s. The wet film was dried at 100° C. for 60 minutes and then was calcined in a muffle roaster for 1, 2, 3, 4, 6, and 8 hours. Afterwards, the substrate was cooled to the room temperature to thereby obtain a series of $TiO_2$ crystalline thin films.

Table 1 shows the crystallite size of $TiO_2$ and the contents of Fe species in thin films that were calcined for different periods of time at 500° C.

TABLE 1

| Calcination Time (h) | Fe2p3(Fe$^{3+}$)$^a$ | Fe2p3(Fe$^{2+}$)$^a$ | Crystallite (nm) |
|---|---|---|---|
| 1 | 3.18% | 0.34% | 9.43 |
| 3 | 4.32% | 0.40% | 9.77 |
| 8 | 5.48% | 1.21% | 10.28 |

Polycrystalline X-ray diffraction patterns of TiO$_2$ thin films on stainless steel calcined for different periods of time in this Example were shown in FIG. 1.

Figure 2:
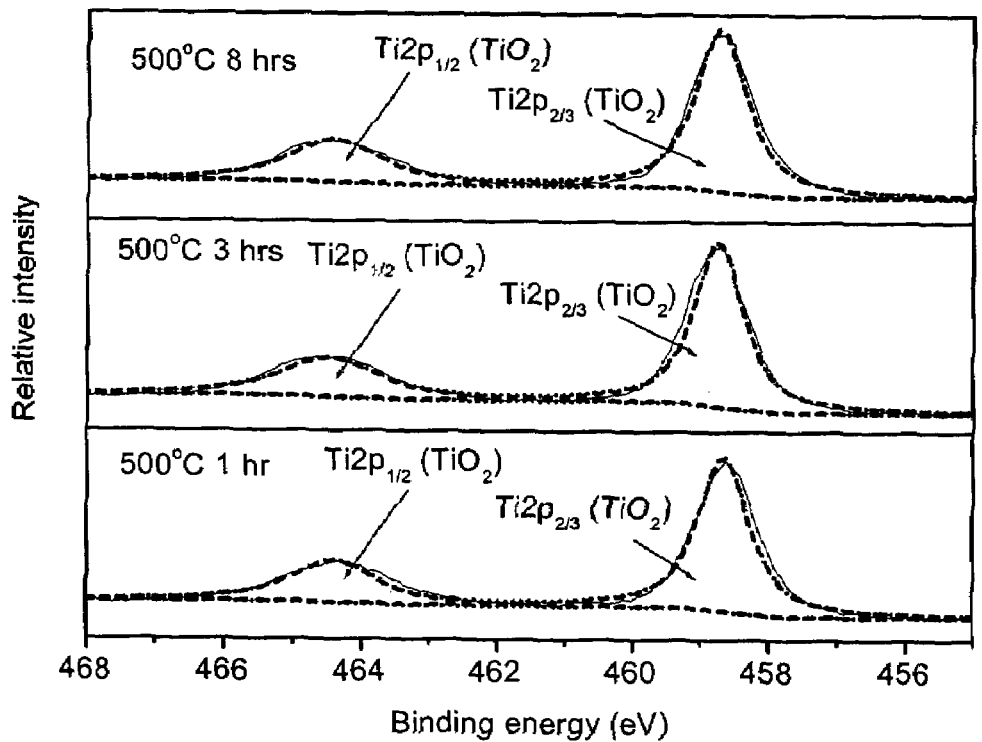
FIG. 2 is X-ray photoelectron spectra of Ti in thin films of the present invention on stainless steel calcined for different periods of time.

X-ray photoelectron spectra of Ti in thin films on stainless steel calcined for different periods of time in this invention were shown in FIG. 2.

Figure 3:
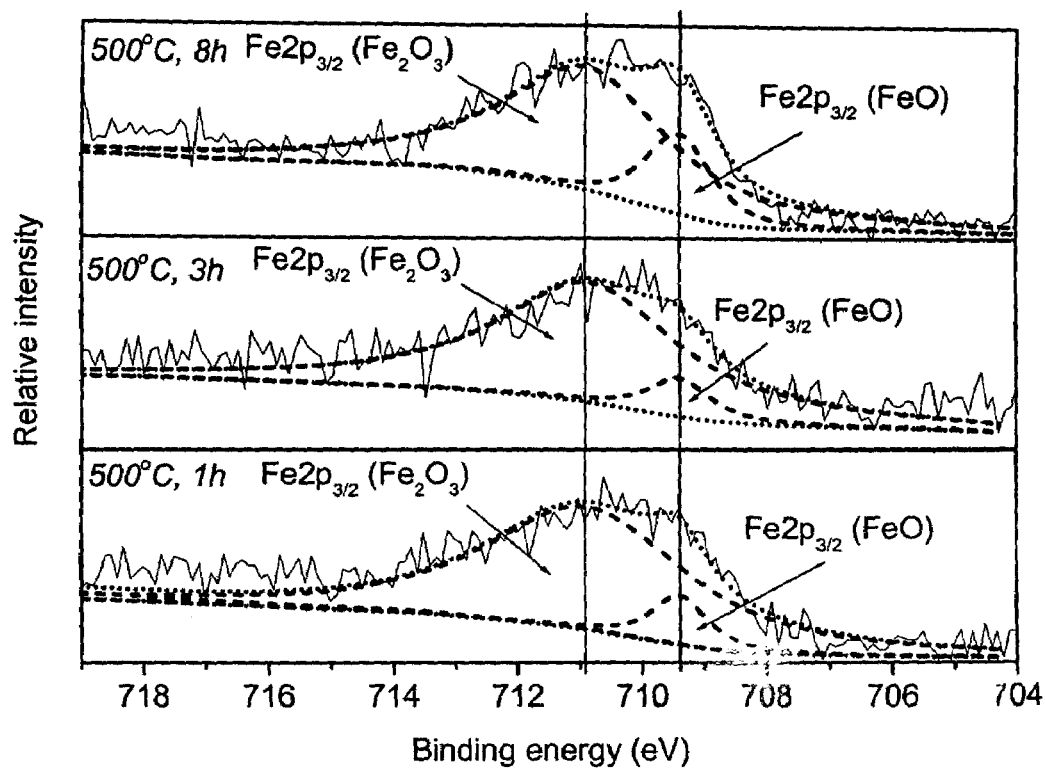
FIG. 3 is X-ray photoelectron spectra of Fe in thin films of the present invention on stainless steel calcined for different periods of time.

X-ray photoelectron spectra of Fe in thin films on stainless steel calcined for different periods of time in this Example were shown in FIG. 3.

Figure 4:
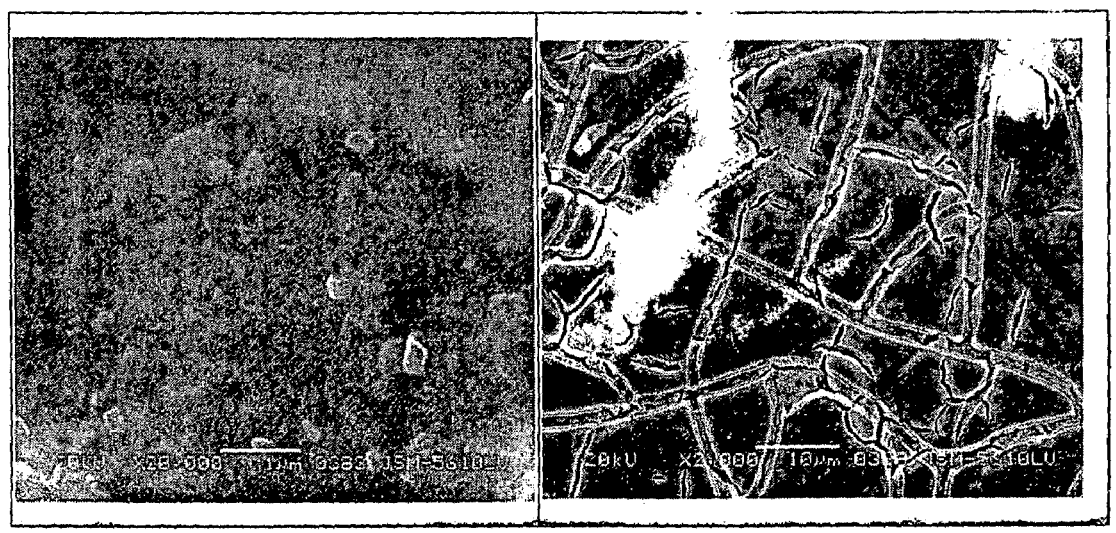
FIG. 4 is a scanning electron microscope image of a thin film of the present invention on stainless steel calcined at 500° C. for 3 hours.

A scanning electron microscope image of a thin film on stainless steel calcined at 500° C. for 3 hours in this Example was shown in FIG. 4.

Example 2

Preparation of TiO$_2$ Thin Films on the Surface of Glass

Thin films onto glass were prepared in the same manner as described in Example 1, except that stainless steel is replaced with glass, and thin films were calcined for 3 hours.

Experimental Example 1

The photocatalytic activity of TiO$_2$ thin films was evaluated by the degradation of acetone in air. The area of TiO$_2$ thin films used for each experiment was 140 cm$^2$ in a 7,000 ml reactor. Before switching on the ultraviolet source, the equilibrium concentration of acetone was controlled at 400±1 ppm, and the initial concentration of water vapor was adjusted to 1.2±0.01 vol %, and the temperature was regulated at 25±1° C. The ultraviolet was generated by a 15 W 365 nm UV lamp (Cole-Parmer Instrument Co.). The concentrations of carbon dioxide, water vapor and acetone were measured on line with a Photoacoustic IR Multigas Monitor (INNOVA Air Tech Instruments Model 1312, Denmark). The total analysis time for each thin film sample was 100 minutes.

Figure 5:
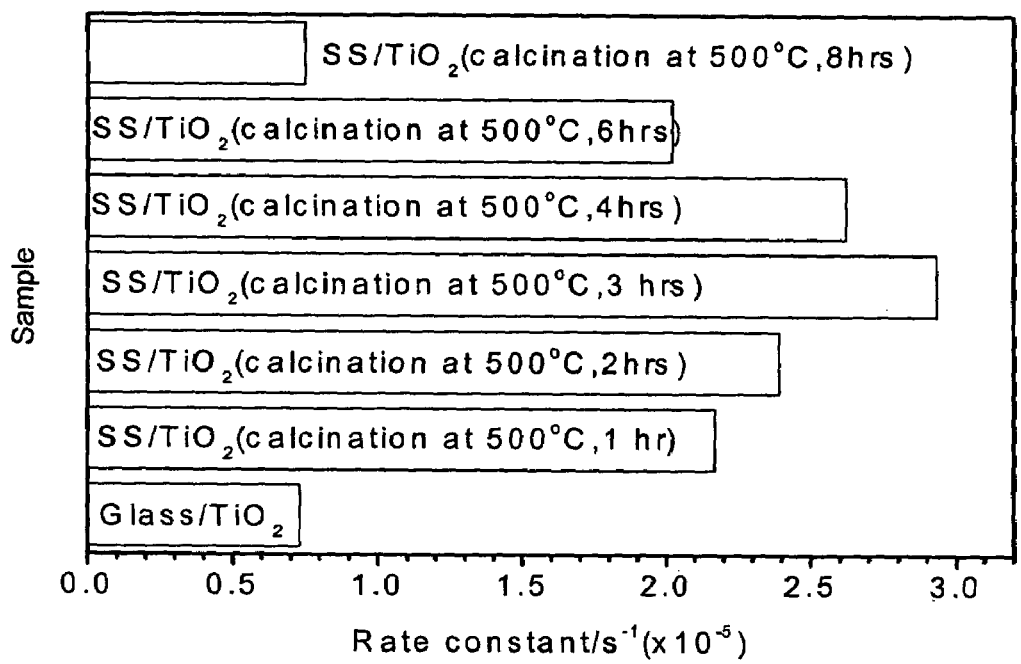
FIG. 5 shows photocatalytic activities of thin films of the present invention on stainless steel calcined for different periods of time.

The thin films prepared in Examples 1 and 2 were analyzed using the above procedure, and results thereof were shown in FIG. 5. FIG. 5 illustrates that the photocatalytic activity of a TiO$_2$ thin film on stainless steel was 3 folds as much as that on glass.

Experimental Example 2

Photocatalytic Antibacterial Activity of TiO$_2$ Thin Films

Figure 6:
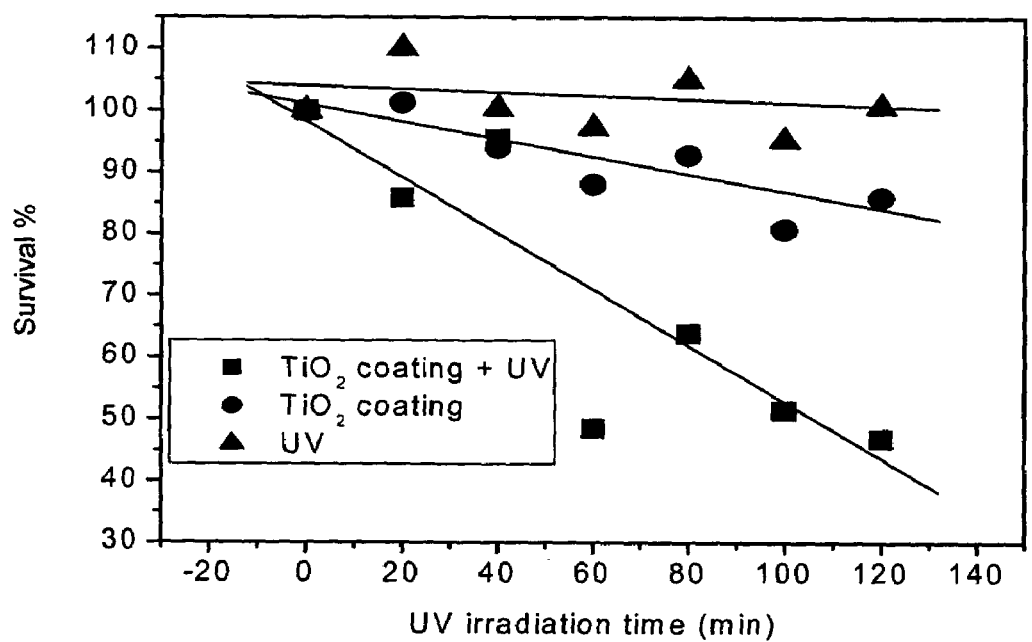
FIG. 6 shows the photo-induced antibacterial effect of thin films of the present invention on stainless steel calcined for different periods of time.

Photocatalytic antibacterial activity of TiO$_2$ thin film was evaluated by killing *Bacillus pumilusi* in an aqueous solution under ultraviolet irradiation. 2 ml of an aqueous solution of *Bacillus pumilusi* having a concentration of 1×10$^7$ CFU/ml was pipetted onto the TiO$_2$ thin film on stainless steel as prepared in Example 1 (calcined for 3 hours). The stainless steel was illuminated by a 15 W 365 nm UV lamp (Cole-Parmer Instrument Co.) at a light intensity of 0.63 mW/cm$^2$. 20 or 40 µl aliquots of serially diluted solutions containing *Bacillus pumillusi* were dispensed into 1 ml of phosphate buffer. Resultant solutions were plated on Luria-Bertani (LB) agar plates at 10 or 20 min intervals. The plates were then incubated at 37° C. for 24 h, and the number of colonies on the plates was counted. The change in the number of bacteria on the surface TiO$_2$ thin films on stainless steel was calculated. Results were shown in FIG. 6.

Experimental Example 3

Hydrophilicity of TiO$_2$ Thin Films

Figure 7:
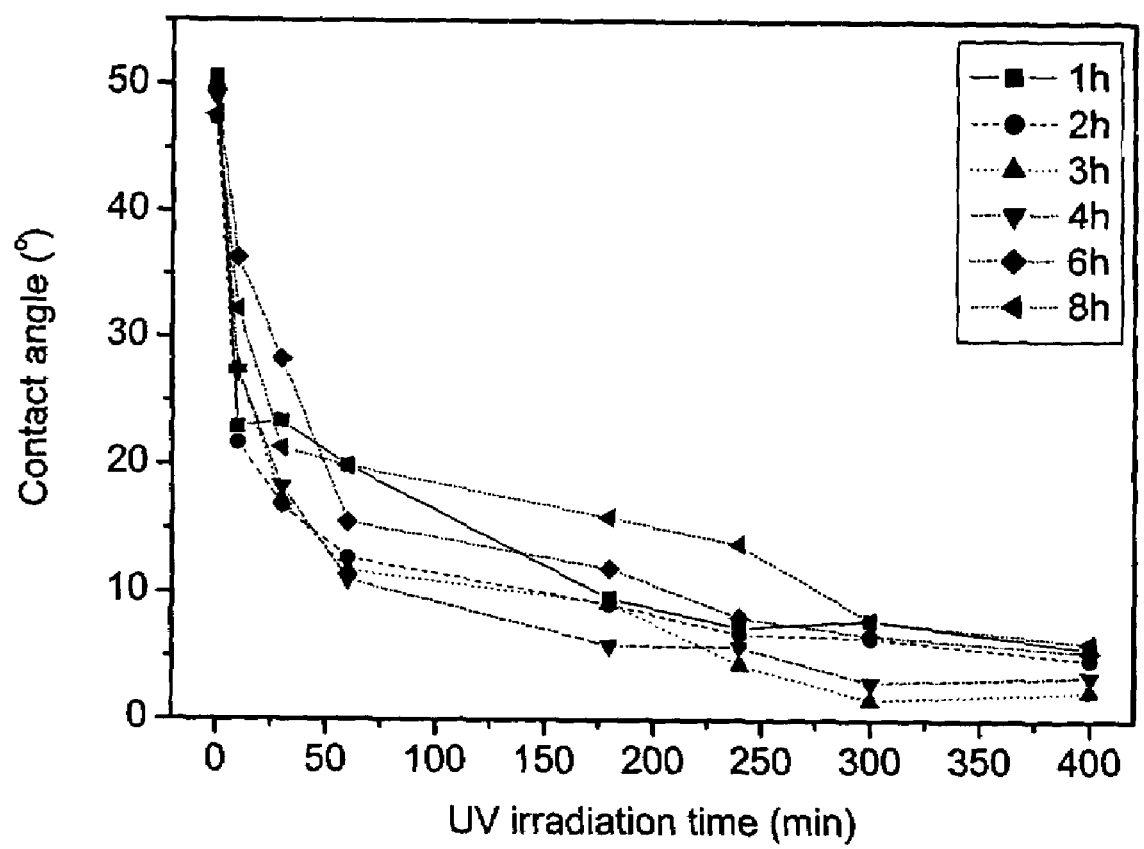
FIG. 7 shows hydrophilicity of thin films of the present invention on stainless steel calcined for different periods of time.

Hydrophilicity of a TiO$_2$ thin film was evaluated with a change of the contact angle between water and the thin film under ultraviolet irradiation (15 W 365 nm, Cole-Parmer Instrument Co.). The contact angle was measured by an instrument, Model CA-XP, Kyowa Interface Science Co. Ltd., Japan. Thin films on stainless steel as prepared in Example 1 were exposed to air for 1 to 2 months to have the contact angle of water on the thin film increased to 50-60°. Then, the thin films were irradiated by ultraviolet light. The results were shown in FIG. 7, which indicated that the contact angle was decreased from 50-60° to around 5° after the thin film was irradiated for 1 hour. It was understood that thin films of the invention had an excellent hydrophilicity.

It is understood that the above Examples and description are only used to illustrate the invention, and that any varieties or modifications to the present invention without departing from the spirit of the invention will be fallen into the scope of the invention which is defined by appended claims.

What is claimed is:

1. A process for preparing a TiO$_2$ thin film having photo-induced antibacterial and antivirus activities comprising the steps of:
    a) providing a reverse micelle solution containing dispersed nano-droplets comprising an organic continuous phase, a non-ionic surfactant, and water;
    b) adding a titanium alkoxide in a concentration from 0.2 to 0.3 M and a stabilizer consisting essentially of a 2,4-diketone in an amount from 2 to 5% by volume of the reverse micelle solution to the reverse micelle solution and subjecting the titanium alkoxide to hydrolysis in said nano-droplets of the reverse micelle solution to form a TiO$_2$-containing solution, wherein said stabilizer controls the rate of hydrolysis of said titanium alkoxide;
    c) forming a wet film onto a substrate dipped into the TiO$_2$-containing solution onto a substrate, wherein the forming step is performed by a dip coating technique; and
    d) drying the wet film and calcining the dried film.

2. The process of claim 1, wherein said organic continuous phase comprises a C$_{3-8}$ alkane; said titanium alkoxide comprises a C$_{1-6}$ alkyl titanate; and said stabilizer is acetyl acetone.

3. The process of claim 2, wherein said organic continuous phase is cyclohexane, and the titanium alkoxide is selected from the group consisting of ethyl titanate, propyl titanate, iso-propyl titanate, n-butyl titanate and iso-butyl titanate.

4. The process of claim 3, wherein said non-ionic surfactant has a molar concentration of 0.15 to 0.4M in the reverse micelle solution.

5. The process of claim 4, wherein said non-ionic surfactant has a molar concentration of 0.2M in the reverse micelle solution.

6. The process of claim 1, wherein step c) is performed with a withdrawal speed of 2-5 mm/s, and step d) is performed with said wet film drying at a temperature ranging from 80° to 120° C. for 0.5 to 1.5 hours and said dried film is calcined at 600° C. for 1 to 6 hours.

7. The process of claim 1, wherein step c) is performed with a withdrawal speed of 2-5 mm/s, and step d) is performed with said wet film drying at a temperature ranging from 80° to 120° C. for 0.5 to 1.5 hours and said dried film calcining at 600° C. for 1 to 6 hours.

8. The process of claim 5, wherein said step c) is performed with a withdrawal speed of 2-5 mm/s, and step d) is performed with said wet film drying at a temperature ranging from 80° to 120° C. for 0.5 to 1.5 hours and said dried film calcining at 600° C. for 1 to 6 hours.

9. The process of claim 8, wherein said dried film is calcined for 3 hours.

10. The process of claim 1, wherein said substrate is selected from the group consisting of metals, glass and ceramics.

11. A process of claim 9, wherein said substrate is selected from the group consisting of metals, glass and ceramics.

12. The process of claim 11, wherein said substrate is stainless steel.

13. The process of claim 1, wherein said non-ionic surfactant comprises a polyols fatty acid ester, a poly oxyethylene aliphatic alcohol ether and/or a polyoxyethylene alkyl phenol ether.

14. A process for preparing a $TiO_2$ thin film having photo-induced antibacterial and antivirus activities comprising the steps of:
   a) providing a reverse micelle solution containing dispersed nano-droplets comprising an organic continuous phase, a non-ionic surfactant, and water;
   b) adding titanium isopropoxide in a concentration from 0.2 to 0.3 M and a stabilizer consisting essentially of a 2,4-diketone in an amount between 1 and 10% by volume of the reverse micelle solution to the reverse micelle solution and subjecting the titanium isopropoxide to hydrolysis in said nano-droplets of the reverse micelle solution to form a $TiO_2$-containing solution, wherein said stabilizer controls the rate of hydrolysis of said titanium alkoxide;
   c) forming a wet film onto a substrate dipped into the $TiO_2$-containing solution onto a substrate, wherein the forming step is performed by a dip coating technique; and
   d) drying the wet film and calcining the dried film.

* * * * *

UNITED STATES PATENT AND TRADEMARK OFFICE
CERTIFICATE OF CORRECTION

| | | |
|---|---|---|
| PATENT NO. | : 7,638,555 B2 | |
| APPLICATION NO. | : 10/688504 | |
| DATED | : December 29, 2009 | |
| INVENTOR(S) | : Chai-Mei Jimmy Yu et al. | |

It is certified that error appears in the above-identified patent and that said Letters Patent is hereby corrected as shown below:

Title Pg, (*) Notice: delete "777" and insert --957--.

On Sheet 1 of 4 (FIG. 1), please change "st el" to --steel--.

At column 2, line 13, please change "decompose" to --decomposes--.

At column 4, line 55, please change "homogeneous" to --homogenous--.

At column 4, line 59, please change "or" to --of--.

At column 4, line 61, after "roaster" please insert --respectively--.

At column 5, line 58, please change "pumilusi" to -- pumilus--.

At column 5, line 60, please change "pumilusi" to --pumilus--.

At column 5, line 66, please change "pumillusi" to --pumilus--.

At column 6, line 66, in Claim 6, after "film" please delete "is".

At column 7, line 6, in Claim 8, after "wherein" please delete "said".

At column 7, line 17, in Claim 11, please change "metals," to --metal,--.

Signed and Sealed this

Seventh Day of September, 2010

David J. Kappos
*Director of the United States Patent and Trademark Office*